United States Patent [19]

Ogawa et al.

[11] Patent Number: 4,834,745
[45] Date of Patent: May 30, 1989

[54] SUSTAINED-RELEASE DISPENSER OF SEX PHEROMONE OF INSECTS

[75] Inventors: Kinya Ogawa, Kawasaki; Akira Yamamoto, Johetsu; Noboru Aiba, Johetsu; Shigehiro Nagura, Johetsu, all of Japan

[73] Assignee: Shin-Etsu Chemical Co., Ltd., Tokyo, Japan

[21] Appl. No.: 29,950

[22] Filed: Mar. 25, 1987

[30] Foreign Application Priority Data

Mar. 25, 1986 [JP]  Japan ................................. 61-66498

[51] Int. Cl.$^4$ ......................... A61K 9/22; A01N 17/00
[52] U.S. Cl. .................................. 604/890.1; 424/405
[58] Field of Search ............ 604/890.1; 424/DIG. 10, 424/405, 408, 84

[56] References Cited

U.S. PATENT DOCUMENTS

| | | | |
|---|---|---|---|
| 3,919,329 | 11/1975 | Anderson et al. ................... | 568/596 |
| 4,017,030 | 4/1977 | Coplan et al. .......................... | 239/44 |
| 4,325,941 | 4/1982 | Dol Moro et al. .................... | 424/84 |
| 4,404,185 | 9/1983 | Maccone et al. ...................... | 424/84 |
| 4,600,146 | 7/1986 | Ohno ................................... | 428/905 |
| 4,601,893 | 7/1986 | Cardinal .............................. | 424/424 |
| 4,639,393 | 1/1987 | von Kohorn et al. ................. | 424/83 |

OTHER PUBLICATIONS

Yamamoto et al., "Sex Pheromone Substance Releasing Tube" Patent Abstracts of Japan, vol. 6, No. 73, May 8, 1982.

Yamamoto et al. "Releasing Tube of Sex Pheromone Substance" Patent Abstracts of Japan, vol. 6, No. 154, Aug. 14, 1982.

Oono, "Gradual Vapor Releaser with Good Shaping Property", Patent Abstracts of Japan, vol. 6, No. 266, Dec. 25, 1982.

Primary Examiner—C. Fred Rosenbaum
Assistant Examiner—Sharon Rose
Attorney, Agent, or Firm—Oblon, Fisher, Spivak, McClelland & Maier

[57] ABSTRACT

The invention provides a dispenser form for substainedly releasing vapor of a sex pheromone compound of pest insects with an object to control the population of the insects. The invention dispenser is characterized by the features that: the capacity thereof is sufficiently large to contain at least 100 mg of the pheromone; the barrier wall thereof through which the pheromone permeates to be released from the outer surface is made of a polymeric material swellable with the pheromone in an equilibrium swelling of 2–6% by weight at 20° C.; and the outer surface area S thereof given in $mm^2$ is sufficient to give a ratio S/W, W being the amount of the pheromone contained therein given in mg, in the range from 4 to 11. The rate of pheromone emission from the dispenser is relatively constant at 0.6 mg/day or larger over a long period of time of, for example, 3 months or longer.

7 Claims, No Drawings

SUSTAINED-RELEASE DISPENSER OF SEX PHEROMONE OF INSECTS

BACKGROUND OF THE INVENTION

The present invention relates to a sustained release dispenser of sex pheromone of insects or, more particularly, to a dispenser capable of sustainedly releasing a sex pheromone of an insectan pest at a constant or controlled rate over a long period of time to control the population of the insect species.

It has been an important technical problem to develop a method for sustainedly releasing a sex pheromone compound of an insectan pest of a particular species at a constant rate over a long period of time into the field. For example, it is already practiced to prepare a dispenser form containing a sex pheromone compound from which the sex pheromone compound is vaporized and emitted at a controlled rate. It would be a desirable ideal if the rate of the pheromone emission could be maintained at a level to exhibit the desired effect over a necessary length of time under meteorologically different conditions such as temperature, humidity, wind velocity and the like. When dispenser bodies having barrier walls made of the same polymeric material are used for enclosing different sex pheromone compounds, however, no satisfactory results can be obtained in respect of the rate of emission for all kinds of the pheromone compounds since the rate of pheromone emission may be too large for one sex pheromone compound while the rate may be too small for the other.

When the rate of pheromone emission from a dispenser is too large, the serviceable life of the dispenser form is naturally unduly short. When the rate of emission is too small, an economical disadvantage may be caused because a considerable portion of the sex pheromone compound initially contained in the dispenser form may be left unutilized therein still after expiration of the necessary length of time.

An unduly short serviceable life of a dispenser form may cause an uneconomically large consumption of man power since distribution of the dispenser forms over the field must be repeated several times during a season in which the effect of the sex pheromone compound should be continuedly exhibited. Moreover, a serious problem may be sometimes caused that the desired effect of the pheromone compound can no longer be exhibited entirely at the latest stage of the serviceable life of the dispenser form due to exhaustion of the pheromone compound contained in the dispenser form.

It is of course that the number of the dispenser forms of a sex pheromone compound to be distributed over a unit area of the field should desirably be as small as possible provided that the effect of the pheromone compound is not affected so much. Unfortunately, no dispenser form has yet been developed which can maintain the necessary rate of pheromone emission over the season even by a single time of distribution of a relatively small number of the dispenser forms in the field.

The inventors have previously developed a dispenser form for sustainedly releasing a sex pheromone compound of insects prepared by filling a polyethylene-made tube having an inner diameter of 0.8 mm, outer diameter of 1.45 mm and length of 200 mm with the sex pheromone compound and performed a field test by using a number of such dispensers (U.S. Pat. No. 4,600,146). In the field test undertaken in the State of Arizona, U.S.A., with an object to control the population of pink bollworms, 894 dispensers, each filled with 72 mg of Z,Z/E-7,11-hexadecadienyl acetate as the sex pheromone of the insects, were distributed per hectare of the field. In this case, the rate of pheromone emission was constantly maintained at about 0.6 mg/day for each dispenser over a period of about 30 days to exhibit sufficiently high effects of intercommunication disruption between different sexes of the insects. Unfortunately, the rate of pheromone emission was decreased to 0.4 mg/day or below for each dispenser after lapse of 50 days so that the desired effect of intercommunication disruption could no longer be fully exhibited [Journal of Economic Entomology, volume 78, No. 6, pages 1431–1436 (1985)].

SUMMARY OF THE INVENTION

An object of the present invention is therefore to provide a novel dispenser form for sustainedly releasing a sex pheromone compound of insects at a constant rate over a period of 3 months or even longer into the field.

Thus, the present invention provides a dispenser containing a sex pheromone compound of a species of insects to sustainedly release the sex pheromone compound to permeate a barrier wall made of a polymeric material and to be released out of the outer surface of the dispenser, having a capacity sufficient to contain at least 100 mg of the sex pheromone compound and having an outer surface area of S $mm^2$, the ratio of S to the amount W in mg of the sex pheromone compound contained therein, i.e. S/W, being in the range from to 11, of which the equilibrium swelling of the polymeric material forming the barrier wall with the sex pheromone compound contained therein is in the range from 2 to 6% by weight at 20° C.

DETAILED DESCRIPTION OF THE PREFERRED EMBODIMENTS

The dispenser of the invention for sustainedly releasing a sex pheromone compound of insects is in a tubular form and has a barrier wall made of a polymeric material through which the sex pheromone compound contained therein permeates and is released from the outer surface into the atmosphere at a constant rate over a length of time.

The serviceable life of the inventive dispenser form for sustainedly releasing the sex pheromone compound depends on the selection of the polymeric material forming the barrier wall to match the respective sex pheromone compound and the dimensions of the dispenser.

It is essential in the inventive dispenser that the polymeric material forming the barrier wall should be swellable with the sex pheromone compound contained therein in an equilibrium swelling in the range from 2 to 6% by weight at 20° C. It is also essential in respect of the dimensions that, assuming that the dispenser has an outer surface area of S $mm^2$ and the amount of the sex pheromone compound contained therein is W mg, the ratio of S/W should be in the range from 4 to 11. The desired stability in the emission rate of the sex pheromone compound is obtained only when these requirements are satisfied to give 3 months or longer of the serviceable life of the dispenser. It is presumable that the above mentioned field test in Arizona could give no fully satisfactory results because the dispensers used in the test had the S/W value of 12.7 outside the above mentioned range which is essential to obtain a constant emission rate of the sex pheromone compound over a long period of time.

When the outer surface area S of the dispenser is too large to give a value of S/W smaller than 11, the rate of pheromone emission would be excessively large with a large difference between the initial and latest stages of the serviceable life of the dispenser so that the serviceable life would be unduly decreased. When the value of S/W is too small, on the other hand, the rate of pheromone emission would be too low so that the desired concentration of the sex pheromone compound cannot be maintained in the atmosphere over the field.

The equilibrium swelling of the polymeric material making the barrier wall can be determined by immersing chips of the polymeric material in the sex pheromone compound and measuring weight increase of the chips at equilibrium. The value of equilibrium swelling thus determined is a determinant factor for the concentration of the sex pheromone compound in the barrier walls of the dispenser.

Assuming that the concentration of the sex pheromone compound in the ambient atmosphere around the dispenser is negligibly small, the rate of vaporization $\Delta M$ of the sex pheromone compound at a temperature $t°$ C. can be expressed as a function of $P_t.S.C$, in which $P_t$ is the vapor pressure of the sex pheromone compound at $t°$ C., S is the outer surface area of the dispenser and C is the concentration of the sex pheromone compound in the barrier wall Namely, $P_t$ is a value inherent in the respective sex pheromone compound, S is a value determined by the dimensions of the dispenser and C is a value determined by the combination of the sex pheromone compound and the polymeric material forming the barrier wall. When the kind of the sex pheromone compound and the dimensions of the dispenser form are given, accordingly, the concentration C of the sex pheromone compound in the barrier wall is the determinant factor for the vaporization rate of the sex pheromone compound from the dispenser.

In other words, the value of C provides a means for estimating the serviceable life of the dispenser. In the inventive dispenser, the rate of pheromone emission can be controlled at a constant level over a long period of time even when the amount of the sex pheromone compound contained in a dispenser is 100 mg or larger to give an appropriate length of the serviceable life of the dispenser by adequately selecting the above mentioned S/W value and the equilibrium swelling of the polymeric material forming the barrier wall with the sex pheromone compound.

The equilibrium swelling of the polymeric material with the sex pheromone compound should preferably be in the range from 2 to 6% by weight at 20° C. When the equilibrium swelling of the polymeric material is smaller than 2% by weight, the rate of pheromone emission would be unduly low while, on the other hand, an equilibrium swelling larger than 6% by weight would give an undesirably large rate of pheromone emission.

The equilibrium swelling of a polymeric material is a parameter determined by the kind of the polymeric material and the solubility parameter and molar volume of the sex pheromone compound Polymeric materials suitable for use in the invention include polyethylene, polypropylene, copolymers of ethylene and vinyl acetate, polyvinyl chloride, cellulose acetate, formalized polyvinyl alcohol and the like, of which polyethylene and copolymers of ethylene and vinyl acetate containing 20% by weight or smaller amount of vinyl acetate are particularly preferred.

The sex pheromone substance contained in the inventive dispenser can be a single compound having activity as a sex pheromone or can be a mixture of two kinds or more of such compounds. When the sex pheromone compound is susceptible to photochemical decomposition by exposure to ultraviolet light, the photochemical decomposition may be decreased by forming the barrier wall of a polymeric material admixed with an ultraviolet absorber, dye or pigment or by admixing the sex pheromone compound per se wit an ultraviolet absorber or antioxidant. It is further optional that the sex pheromone compound contained in the dispenser is blended with a filler or diluted with a solvent according to need.

Though not particularly limitative, the inventive dispenser for sustainedly releasing a sex pheromone compound should be in a spherical, ellipsoidal, cylindrical or platelike form having a hollow space surrounded by the barrier walls made of the polymeric material to contain the sex pheromone compound therein. A preferable form of the dispenser is a capillary tube having an inner diameter of 0.8 mm or larger sealed by welding at both ends It is further optional that the inventive dispenser has other modified configuration in order to facilitate engaging or hanging of the dispensers to or on the tree twigs in orchards. For example, it is a possible way that two or more of the dispensers each in the form of a capillary tube and containing a different sex pheromone compound from the others are combined together and used as an integral body.

According to the invention, each of the dispensers can emit the sex pheromone compound contained therein at a constant rate of 0.6 mg per day even after lapse of three months or longer. Accordingly, the inventive dispensers for sustainedly releasing a sex pheromone compound provide a means to give a sufficient effect of intercommunication disruption between different sexes of the insects throughout the season by a single time of the installation works with a relatively small distribution density thereof over the field in the range of, for example, from 200 to 1500 per hectare.

Moreover, the present invention provides a means to obviate the difficult problem in the prior art that, when a dispenser contains a large amount, e.g. 100 mg or larger, of the sex pheromone compound, the rate of pheromone emission therefrom greatly differs between the former half and latter half of the serviceable life of the dispenser.

In the following, examples are given to illustrate the inventive dispenser forms in more detail but not to limit the scope of the invention in any way.

EXAMPLE 1

A 120 mg portion of Z,Z/E-7,11-hexadecadienyl acetate as the sex pheromone of pink bollworms was introduced into a capillary tube of high-density polyethylene having an outer diameter of 2.3 mm, inner diameter of 1.5 mm and length of 80 mm and the tube was sealed by welding at both ends to give a dispenser of the sex pheromone compound. The outer surface area of this dispenser form S was 580 mm² so that the value of S/W was equal to 4.8. A chip of the same high-density polyethylene having dimensions of 20 mm by 20 mm by 1 mm was immersed in the sex pheromone compound at 20° C and the equilibrium swelling of the polymer in the pheromone compound was determined from the weight increase of the chip to give a value of 2.9% by weight.

The dispenser was kept in an air stream at a velocity of 0.5 meter/second at 30° C and the rate of pheromone emission therefrom was calculated from the weight decrease of the dispenser. The results were that the rate was 0.96 mg/day, 0.72 mg/day, 0.64 mg/day or 0.52 mg/day after lapse of 30 days, 60 days, 90 days or 120 days, respectively. The amount of the pheromone compound left unreleased in the capillary tube was 24 mg after 120 days. Thus, it was concluded that the inventive dispenser could release the sex pheromone compound at a quite satisfactorily uniform rate over a long period of almost four months.

EXAMPLE 2

A dispenser was prepared in a similar manner to Example 1 containing 120 mg of E,E-8,10-dodecadienol as the sex pheromone of codling moths. The capillary tube in this case was made of a copolymer of 97% ethylene and 3% vinyl acetate and had an outer diameter of 1.60 mm, inner diameter of 0.96 mm and length of 200 mm. The outer surface area S of the thus prepared dispenser was 1005 mm$^2$ so that the value of S/W was equal to 8.4. The equilibrium swelling of the copolymer in the sex pheromone compound was 3.2% by weight.

The rate of pheromone emission over days was determined in the same manner as in Example 1 to give the results of 1.08 mg/day, 0.75 mg/day, 0.62 mg/day and 0.44 mg/day after lapse of 30 days, 60 days, 90 days and 120 days, respectively, so that it was concluded that the rate of pheromone emission was at least 0.6 mg/day over 90 days or longer.

What is claimed is:

1. A device for the sustained release of vapor of a sex pheromone of an insect comprising a dispenser in a spherical, ellipsoidal cylindrical or plate-like form having a hollow space surrounded by barrier walls, wherein said dispenser is made of a polymeric material selected from the group consisting of polyethylene, polypropylene, an ethylyene-vinyl acetate copolymer, polyvinyl chloride, cellulose acetate and formalized polyvinyl alcohol and containing a sex pheromone compound which is released from the outer surface there of in the form of a vapor, wherein the capacity of the dispenser is sufficiently large to contain at least 100 mg of the sex pheromone compound, the polymeric material is swellable with the sex pheromone compound in a equilibrium swelling in the range from 2 to 6% by weight at 20° C., and the ratio S/W is in the range from 4 to 11, where S is the outer surface area of the dispenser expressed in mm2 and W is the amount of the sex pheromone compound contained in the dispenser expressed in mg.

2. The device as claimed in claim 1, in which the barrier wall of the dispenser is made of a polymeric material admixed with a UV absorber, a dye or a pigment.

3. The device as claimed in claim 1, wherein the sex pheromone compound is admixed with a UV absorber or antioxidant, blended with a filler or diluted with a solvent.

4. The device as claimed in claim 1, wherein the dispenser is a capillary tube having an inner diameter of at least 0.8 mm and sealed at both ends.

5. The device as claimed in claim 1, comprising two or more dispensers combined together as an integral body.

6. The device as claimed in claim 1, wherein the dispenser is made from high-density polyethylene and the sex pheromone is Z,Z/E-7,11-hecadecadienyl acetate.

7. The device as claimed in claim 1, wherein the dispenser is made from a copolymer of 97% ethylene and 3% vinyl acetate and the sex pheromone is E,E,8,10-dodecadienol.

* * * * *